United States Patent [19]

Kessler et al.

[11] 4,411,151

[45] Oct. 25, 1983

[54] DEVICE FOR CALIBRATING GAS ELECTRODES

[75] Inventors: Manfred Kessler, an den Harindicsm 50, 8520 Erlangen, Fed. Rep. of Germany; Jens Höper, Erlanngen, Fed. Rep. of Germany

[73] Assignee: Manfred Kessler, Erlangen, Fed. Rep. of Germany

[21] Appl. No.: 258,725

[22] Filed: Apr. 29, 1981

[51] Int. Cl.³ .......................................... G01N 33/48
[52] U.S. Cl. ..................................................... 73/1 G
[58] Field of Search ............ 73/1 G, 23; 128/132 D, 128/719, 204.22

[56] References Cited

U.S. PATENT DOCUMENTS

| | | | |
|---|---|---|---|
| 3,924,442 | 12/1975 | Kerho et al. | 73/1 G |
| 3,985,633 | 10/1976 | Lubbers et al. | 204/412 |
| 4,164,941 | 8/1979 | Knopick et al. | 128/132 D |
| 4,269,057 | 5/1981 | Ong et al. | 73/1 G |
| 4,321,113 | 3/1982 | Grambow et al. | 73/1 G |
| 4,334,529 | 6/1982 | Wirth | 128/132 D |

*Primary Examiner*—Stephen A. Kreitman
*Attorney, Agent, or Firm*—Michael J. Striker

[57] ABSTRACT

A device for calibrating gas electrodes inserted into a gas testing container within sterile environment of an operation room is mounted on a movable frame and has one side to be sterilized and carrying a work table with the gas testing container and another side at which a nonsterile person operates. A gas supply unit is mounted on another side of the frame. Those two sides are separated from each other by a yoke which supports gas hoses extended between the gas testing container and the gas supply unit.

3 Claims, 2 Drawing Figures

DEVICE FOR CALIBRATING GAS ELECTRODES

BACKGROUND OF THE INVENTION

The invention relates to a device for calibrating gas electrodes.

The measuring of gas partial pressures in organic tissue find increasing use in medicine, because physiological conditions of the total organism, as well as the logic organism can be defined with great assurance, so that, in particular during surgery better supervisions are made possible.

The electrodes of gas analysers used for measuring gas pressures are very sensitive in their function, so that it is very often required to restore the electrodes immediately before use. However, this must take place in the sterile environment of the operation room, because the electrode is applied to the patient after preparation.

SUMMARY OF THE INVENTION

In order to provide the possibility to calibrate gas electrodes within the sterile environment of the operation room, the invention provides that a sterilisable calibration chassis is provided, which is connectable to a supply unit by means of hose lines through rapid clutches, as well as a moveable frame which receives the supply unit, whereby the frame is provided with a work table with a yoke for receiving the calibrating chassis which can be covered with cloths.

The advantage of the device consists in that the device is provided for calibrating electrodes in the sterile environment of the operation room. Thereby, the calibration chassis with the hoses and the rapid clutches are sterilized, while the moveable frame remains unsterilized; it is covered, however with sterile cloths. The flow of bacteria from sterile cloths is, as is known, so low, so that the increase of the bacteria amount does not exceed the required value.

The connection of the calibrating chassis is performed in that a sterile person places the calibraing chassis onto the table of the movable frame which table is covered with sterile cloths, and throws the sterile hoses over the yoke of the table to a person on the nonsterile side. This person then performs the connecting of the clutches.

In order to substantially facilitate the handling of the calibrating chassis and to prevent the flow of bacteria through the gas lines one or a plurality of throttle valves are provided on a calibrating container which is mounted on the calibrating chassis, whereby thermostatized liquid flows through rapid clutches and hoses into the calibrating container and into which calibrating gas can be fed from beneath through a gas line by means of a water volume standing above a batch, the outputs of the throttle valves being coupled with the gas line of the calibrating container and the inputs being coupleable with the gas supply containers through bacteria filters, hoses and the rapid clutches.

The advantage of this device consists in that in the calibrating container, into which the prepared electrodes are placed, an atmosphere of moisture saturated calibration gas is present, which is a prerequisite for an exact calibration, that the additional bacterisation of the working area is prevented by filters, and that the gas flow of calibration gas can be easily adjustable from the sterile side.

In order to further improve the handling from the unsterile side, the moveable frame is provided with means for mounting gas supply containers, a thermostat and a connecting plate on which the nonsterile connections of the rapid clutch are mounted.

Due to this arrangement, the manipulation of the connecting of the lines is facilitated and can be performed with one hand, so that any repercussion on the sterile side, displacement or soiling of the sterile cloths, site or position changes of the moveable frame or the supply units, are eliminated.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENTS

Figure 1:
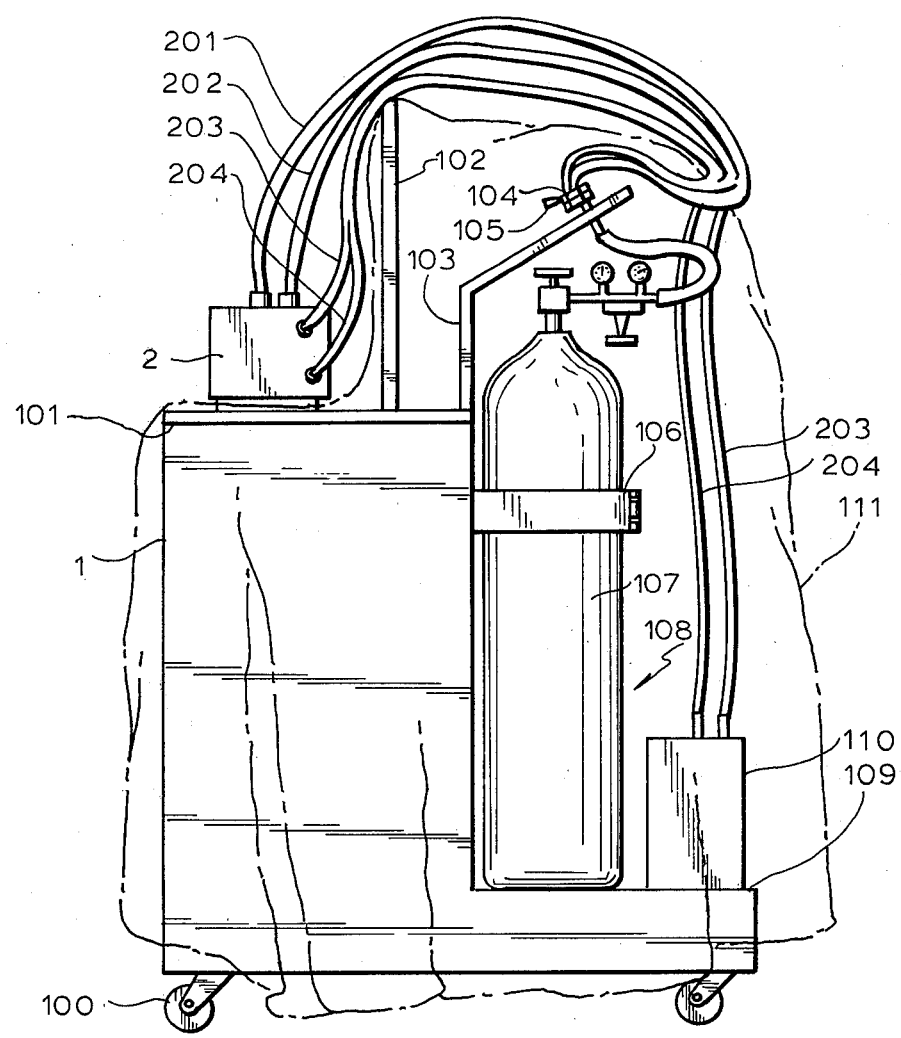
FIG. 1 is a side view of a moveable frame with a calibration chassis and supply devices.

In FIG. 1, on a frame 1 rollers 100 are provided, as well as a table 101 with a yoke 102, a connecting plate 103 with (consecutively disposed) rapid couplings or clutches (clutch 105 is covered), a retaining device 106 for gas supply container 107, 108 (container 108 is covered) and a mounting face 109 of frame 1 for a thermostat 110. The frame is covered with a sterile cloth 111 in such a manner that a calibrating chassis 2 shown as a block can be mounted on table 101 which is covered with the cloth. The yoke 102 which is disposed under cloth 111 provides a support for gas and water hoses 201,202,203,204 which are thrown over the yoke 102 in a sterile condition and are coupled with the nonsterile supply units like gas bottles and thermostats in an nonsterile manner. Thereby, an arrangement is provided which may be nonsterile below cloth 111 and behind yoke 102, but is sterile before the yoke and on the working table. When the calibrating chassis 2 is sterilized, the device can be used in the operating area.

Figure 2:
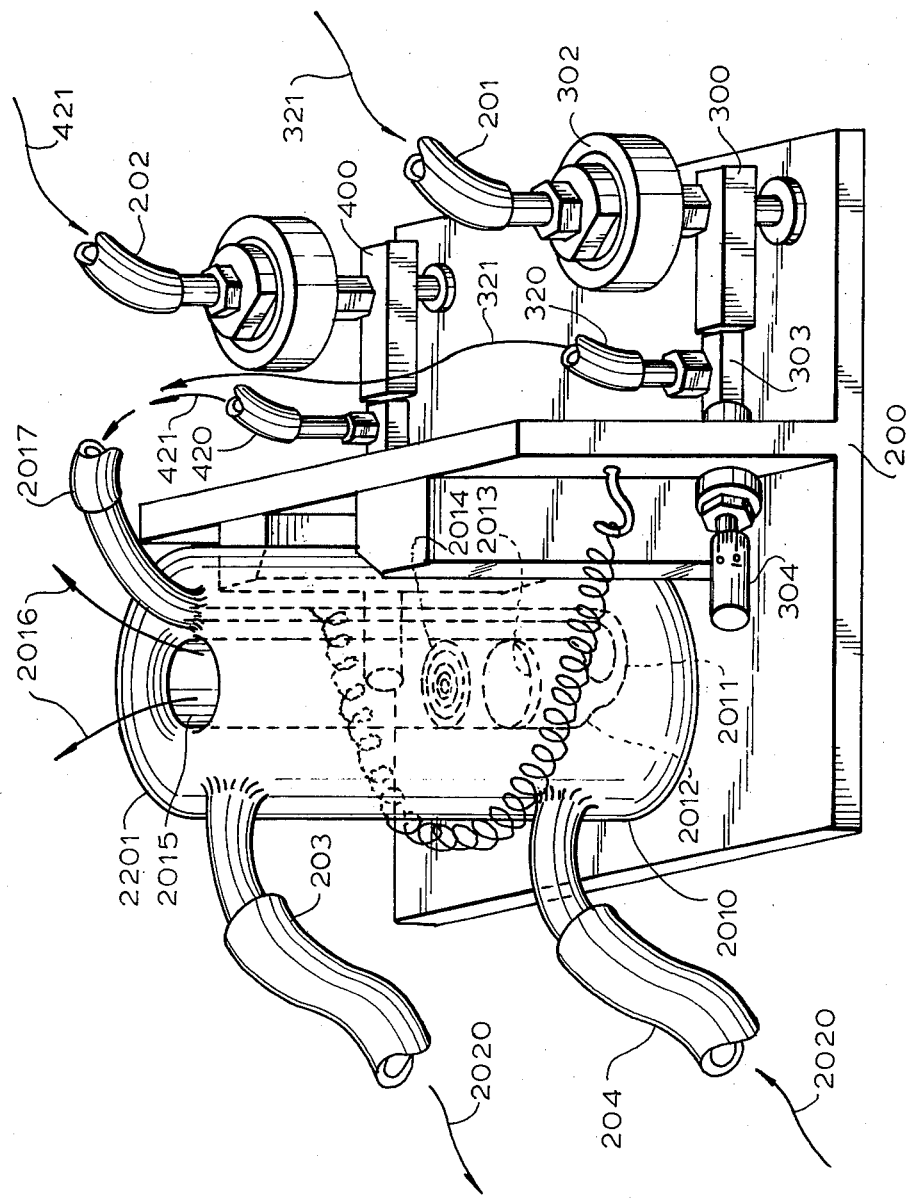
FIG. 2 is a perspective view of the calibration chassis.

A calibrating container 2201 is mounted on a base plate 200 in FIG. 2. It consists of a jacket container 2010 through which thermostatized liquid 2020 flows and through which a gas line 2011 runs which expands toward a testing container 2012. A water volume 2014 for moistening the calibrating gas in container 2201 stands above a batch 2013, and an opening 2015 is provided into which the electrode to be calibrated is inserted and from which the testing gas 2016 escapes. The feeding of the gas is carried out through line 2017 from supply line armatures 300,400. The armatures 300, 400 are the same, so that it suffices to describes armature 300.

The supply of gas is carried out through a line hose 201 from one of the gas supply containers which are mounted on the moveable frame. The gas, which at this time is not bacteria free, passes through a bacteria filter 302, which, as an example, is provided with exchangeable cellulose acetate filters. A finely adjustable throttle valve 303 with calibrated adjustment knob 304 permits the control of the flow quantity in line 320. Line 320 and line 420 of the second armature 400 are fed to the gas line 2017 and back to the calibrating chassis through a suitable T-piece, not shown.

The total device is constructed of materials which permit a sterilisation with hot steam.

For calibration, at first a gas flow is adjusted with adjustment knob 304, so that the gas 321 slowly bubbles through the water volume 2014. After reaching stability, a measuring point is determined by the electrode inserted (here not shown) into the opening 2015, and then a second measuring point is determined in the same manner with the adjustment knob of armature 400 and gas 421. A prerequisite for using the method is the use of two calibrated gases in the supply containers, as well as the knowledge of the calibration curve of the electrodes, so that two calibration points are sufficient for determining the whole scale.

It will be understood that each of the elements described above, or two or more together, may also find a useful application in other types of devices for calibrating gas electrodes differing from the types described above.

While the invention has been illustrated and described as embodied in a device for calibrating gas electrodes, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Device for calibrating gas electrodes within sterile environment of an operation room, comprising a movable frame having one side to be sterilized and another side which remains nonsterile; a work table arranged on said frame at said one side; a calibrating chassis mounted on said table at said one side and carrying a gas calibrating container into which an electrode to be calibrated is inserted; a gas supply unit mounted on said frame at another side thereof; a yoke mounted on said work table and separating said one side from said another side; hoses connected to said gas calibrating container and provided with rapid clutches connectable to said gas supply unit, said another side and said yoke being covered with sterile cloth, said yoke supporting said hoses such that they extend from said one side over said yoke to said another side.

2. Device in accordance with claim 1, further comprising a plurality of throttle valves provided on the calibrating container receiving thermostatized liquid which flows through the rapid clutches and the hoses into the calibrating container and into which a calibrating gas is fed through a gas line, whereby the outputs of the throttle valves are coupled with the gas line of calibrating container and the inputs thereof are coupleable with the gas supply unit through bacteria filters, said hoses (201) and said rapid clutches (104).

3. Device in accordance with claim 2, wherein the moveable frame is provided with means for mounting the gas supply container, a thermostat and a connecting plate on which nonsterile connections of the rapid clutches are mounted.

* * * * *